US012682583B2

(12) United States Patent
Pande et al.

(10) Patent No.: US 12,682,583 B2
(45) Date of Patent: Jul. 14, 2026

(54) SYSTEM AND METHOD FOR VISUALIZING VOLUME LAYERS IN ASSOCIATION WITH AN OBJECT

(71) Applicant: ImmersiveTouch Inc, Westmont, IL (US)

(72) Inventors: Siddhant Pande, Chicago, IL (US); Jia Luo, Chicago, IL (US); Jay Banerjee, Chicago, IL (US)

(73) Assignee: IMMERSIVETOUCH, INC., Chicago, IL (US)

( * ) Notice: Subject to any disclaimer, the term of this patent is extended or adjusted under 35 U.S.C. 154(b) by 170 days.

(21) Appl. No.: 18/584,925

(22) Filed: Feb. 22, 2024

(65) Prior Publication Data

US 2024/0282061 A1     Aug. 22, 2024

Related U.S. Application Data

(60) Provisional application No. 63/447,428, filed on Feb. 22, 2023.

(51) Int. Cl.
| | |
|---|---|
| *G06T 19/00* | (2011.01) |
| *A61B 34/20* | (2016.01) |
| *G06V 40/20* | (2022.01) |
| *G16H 30/40* | (2018.01) |

(52) U.S. Cl.
CPC ............ *G06T 19/006* (2013.01); *A61B 34/20* (2016.02); *G06V 40/20* (2022.01); *G16H 30/40* (2018.01); *A61B 2034/2055* (2016.02); *G06V 2201/07* (2022.01)

(58) Field of Classification Search
USPC ......................................................... 345/633
See application file for complete search history.

(56) References Cited

U.S. PATENT DOCUMENTS

| | | | | |
|---|---|---|---|---|
| 12,602,879 B2 * | 4/2026 | You | ........................ | G06T 19/006 |
| 2022/0287676 A1 * | 9/2022 | Steines | .................. | A61B 90/37 |

* cited by examiner

*Primary Examiner* — Michael J Cobb
(74) *Attorney, Agent, or Firm* — DLA PIPER LLP US

(57) ABSTRACT

Embodiments of the present disclosure provide a system, a method, and a computer programmable product for visualizing volume layers on an object accurately. The system retrieves imaging data relating to an object, generates a set of volume layers corresponding to the object based on the imaging data, and generates a set of guide attributes associated with a virtual guide for the object based on the imaging data. The virtual guide includes an object-specific structure. The system causes to project the virtual guide at least in association with the object and visualizes the set of volume layers in association with the object based on the projected virtual guide.

20 Claims, 7 Drawing Sheets

200A 204                                                    202

200B 204
202
206
208

100B

300C

304

302

306

500

502    RETRIEVE IMAGING DATA RELATING TO AN OBJECT

504    GENERATE A SET OF VOLUME LAYERS BASED ON THE IMAGING DATA

506    GENERATE A SET OF GUIDE ATTRIBUTES FOR A VIRTUAL GUIDE

508    CAUSE TO PROJECT THE VIRTUAL GUIDE IN ASSOCIATION WITH THE OBJECT

510    VISUALIZE THE SET OF VOLUME LAYERS IN ASSOCIATION WITH THE OBJECT BASED ON THE PROJECTED VIRTUAL GUIDE

SYSTEM AND METHOD FOR VISUALIZING VOLUME LAYERS IN ASSOCIATION WITH AN OBJECT

CROSS-REFERENCE TO RELATED APPLICATION

This application claims priority to and the benefit of U.S. Provisional Patent Application No. 63/447,428, filed on Feb. 22, 2023, the contents of which is hereby incorporated by reference herein for all purposes.

TECHNOLOGICAL FIELD

The present disclosure generally relates to multi-dimensional data visualization and interaction in an augmented reality (AR), virtual reality (VR), or mixed reality (MR) environment, and more particularly relates to systems and methods for interaction of a virtual guide in an AR, VR or MR environment for visualization of volume layers.

BACKGROUND

Augmented reality (AR), virtual reality (VR), and mixed reality (MR) are immersive technologies that enable realistic psychological and physical experiences through immersive real-life simulations in a safe environment.

VR technology takes traditional media such as, but not limited to, a photographic image, a video, a sound, and a computer-generated graphics, beyond conventional two-dimensional (2D) screens, and presents them with a three-dimensional (3D), immersive and real-time interactive experience. The AR and MR technologies further enhance a user's perceptions of reality by aligning the physical world with the virtual digital media.

In healthcare, AR/VR/MR technologies enable various data visualization techniques for treatment and diagnostics. Examples of data visualization techniques include, but are not limited to, body mapping, thermal imaging, advanced diagnostics, and digital twin of patient's physical condition. However, visualization of volume layers of a virtual environment accurately with a real or physical environment, such as collocation of volume layers of patient's anatomy on a real patient, may be prone to errors. For example, such errors may arise due to difference in orientation of the patient's anatomy in the volume layers and in the real world. Further, the errors may also arise due to difference in viewpoint of different users observing a same set of volume layers. As a result, accuracy of visualization of virtual volume layers in the real world may be less in a mixed reality or augmented reality environment. Therefore, there is a need to collocate or visualize volume layers in physical or real world accurately with great precision.

SUMMARY

The present disclosure describes a digital guide that may be used in a virtual environment, such as mixed reality environment. Such a digital guide may be used in place of or in combination with a hardware device, such as 3D printed hardware associated with a medical or surgical procedure, to improve the overall accuracy and effectiveness of various imaging related and volume visualization related healthcare procedures.

A system, a method and a computer programmable product are provided herein for collocating volume layers on an object, such as a biological structure of a patient or a surgical equipment, accurately.

In one aspect, a system for visualizing volume layers on an object may be provided. The system may include a memory configured to store computer-executable instructions; and one or more processors configured to execute the computer-executable instructions to retrieve imaging data relating to an object, generate a set of volume layers corresponding to the object based on the imaging data, and generate a set of guide attributes associated with a virtual guide for the object based on the imaging data. The virtual guide includes an object-specific structure. The one or more processors are further configured to cause to project the virtual guide at least in association with the object and visualize the set of volume layers in association with the object based on the projected virtual guide.

In an example, the virtual guide is generated based on three-dimensional (3D) printing of the set of guide attributes in a virtual environment.

In additional system embodiments, the set of guide attributes associated with the virtual guide are aligned with device attributes of at least one of: a tracking object, or a display device.

In additional system embodiments, the one or more processors are further configured to determine, tracking data associated with a user with respect to the object using the tracking object, cause to update the projection of the virtual guide, and visualize the set of volume layers in association with the object based on the updated projection of the virtual guide.

In additional system embodiments, the tracking data of the user comprises at least one of: location data, movement data, orientation data, or gestures data.

In an example, the tracking object is configured to track a pose of the user and further recognize gestures of the user to collect tracking data.

In an example, the one or more processors are configured to visualize or overlay the set of volume layers on the object using the virtual guide, and the tracked pose and the tracked gestures of the user.

In additional system embodiments, the one or more processors are further configured to determine interaction data between a user and the visualized set of volume layers using the tracking object, generate updated set of volume layers for the object based on the imaging data and the interaction data, and visualize the updated set of volume layers in association with the object based on the projected virtual guide.

In additional system embodiments, the one or more processors are further configured to cause to project the virtual guide on a display of the display device associated with a user, visualize the set of volume layers in association with the object based on the projected virtual guide on the display, and cause to display the visualized set of volume layers on the display of the display device.

In additional system embodiments, the display device is at least one of: an augmented reality (AR) head-mountable display device, a virtual reality (VR) head-mountable display device, or a mixed reality (MR) head-mountable display device.

In additional system embodiments, the system further comprises an artificial intelligence (AI) module. Further, the one or more processors are further configured to perform, using the AI module, at least one of: 3D landmark detection or 3D segmentations associated with the object.

In additional system embodiments, the one or more processors are further configured to determine at least one of:

linear measurements, or angular measurements, with respect to at least the virtual guide, the object and the visualization of the set of volume layers.

In additional system embodiments, each layer of the set of volume layers includes a 3-dimensional (3D) or a 2-dimensional (2D) array of voxels based on the imaging data.

In additional system embodiments, the object is a biological structure of a patient.

In additional system embodiments, the imaging data corresponds to source 2D patient scans. Further, the one or more processors are further configured to generate a 3D model of the biological structure of the patient, and visualize the set of volume layers corresponding to the biological structure indicating the source 2D patient scans in association with the 3D model.

In an example, the imaging data may indicate a set of attributes relating to the biological structure of the patient. For example, the imaging data includes patient's medical imaging data. Examples of the medical imaging data may include, but are not limited to, Computed Tomography (CT) data, Computed Tomography Angiography (CTA) data, Magnetic Resonance Imaging (MRI) data, and Magnetic Resonance Angiography (MRA) data.

In additional system embodiments, the virtual guide includes at least one of: a constellation of spheres or other geometric primitives, a two-dimensional (2D) bar code, a constellation of 2D bar codes, a constellation of Quick Response (QR) codes, a 2D image, or a 3D object.

In additional system embodiments, the set of guide attributes corresponding to the virtual guide includes object-specific information.

In additional system embodiments, the one or more processors are further configured to receive marking data relating to the object, wherein the marking data corresponds to a function, visualize the set of volume layers in association with the object based on the virtual guide and the marking data, and cause to perform the function based on the visualized the set of volume layers. The marking data is associated with the virtual guide.

In additional system embodiments, the function is related to at least one of: a surgery operation, a treatment operation, or a diagnostic operation.

In another aspect, a method for visualizing volume layers on an object is provided. The method comprises retrieving imaging data relating to an object, generating a set of volume layers corresponding to the object based on the imaging data, and generating a set of guide attributes associated with a virtual guide for the object based on the imaging data. The virtual guide includes an object-specific structure. The method further comprises causing to project the virtual guide at least in association with the object and visualizing the set of volume layers in association with the object based on the projected virtual guide.

In another aspect, a computer programmable product for visualizing volume layers on an object is provided. The computer programmable product comprises a non-transitory computer readable medium having stored thereon computer executable instructions, which when executed by one or more processors, cause the one or more processors to carry out operations. The operations comprise retrieving imaging data relating to an object, generating a set of volume layers corresponding to the object based on the imaging data, and generating a set of guide attributes associated with a virtual guide for the object based on the imaging data. The virtual guide includes an object-specific structure. The operations further comprise causing to project the virtual guide at least in association with the object and visualizing the set of volume layers in association with the object based on the projected virtual guide.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Figure 1A:
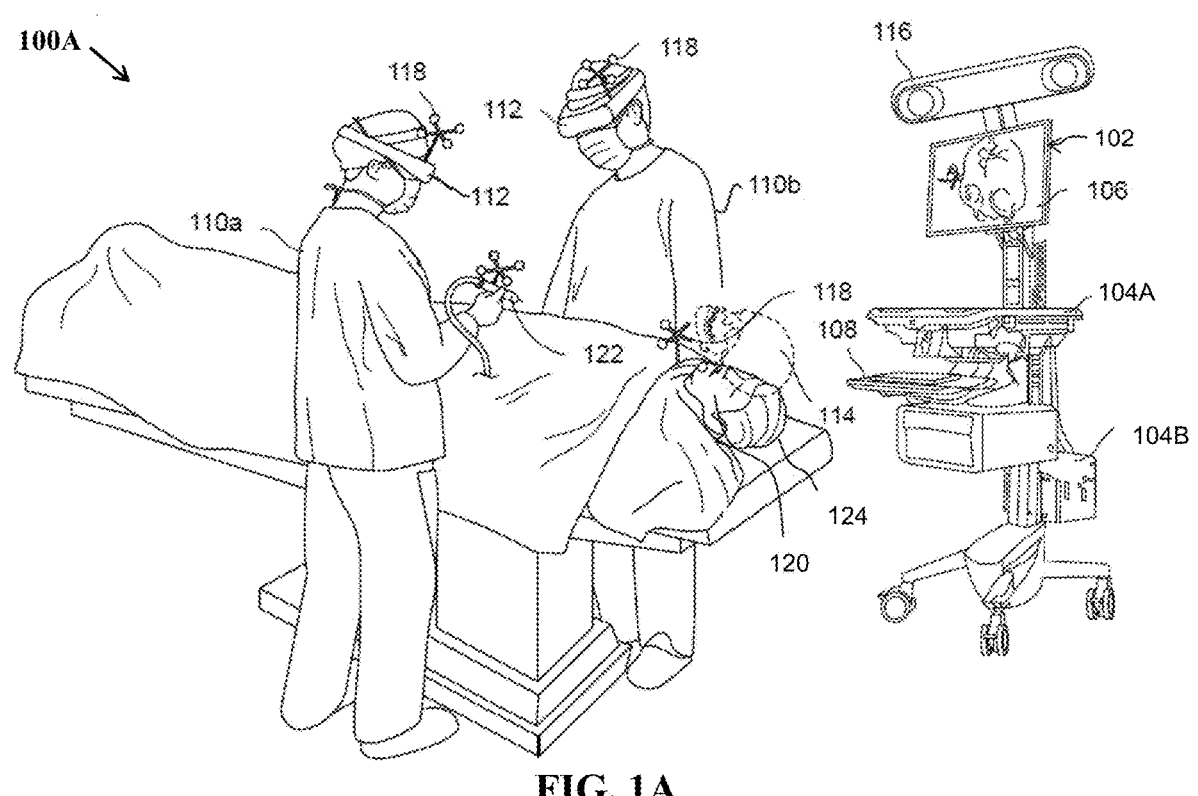
Figure 1B:
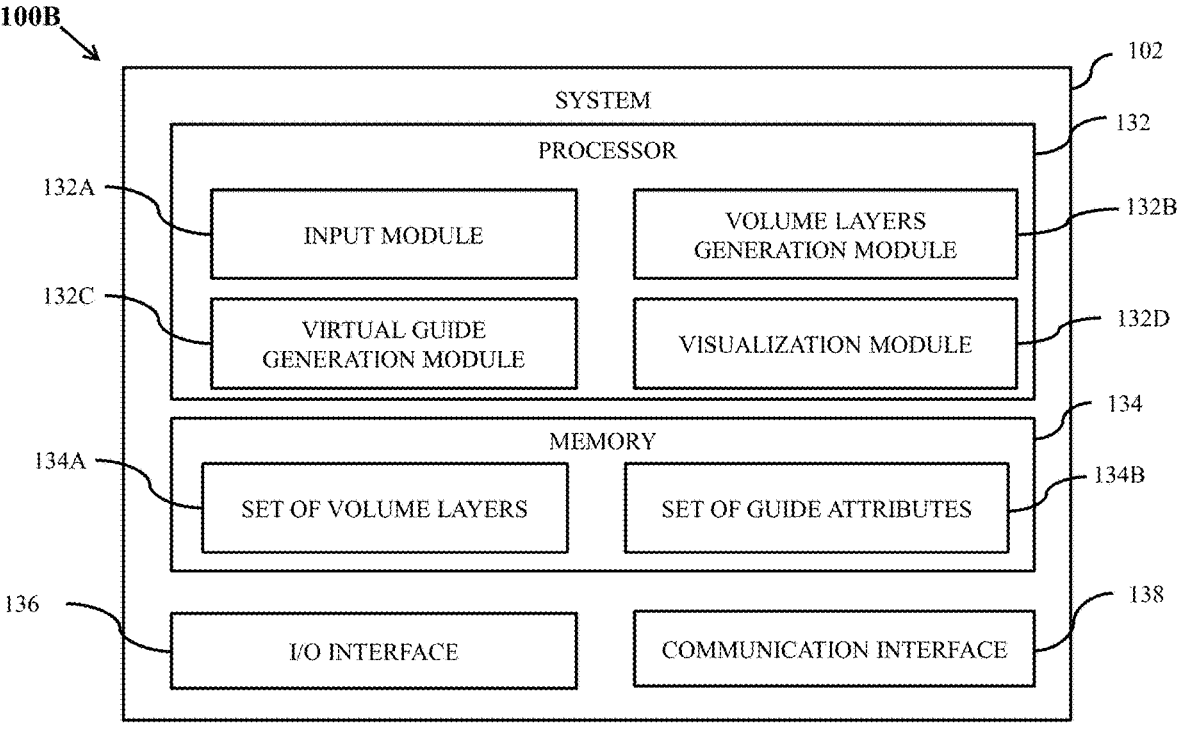
Figures 2A, 2B:
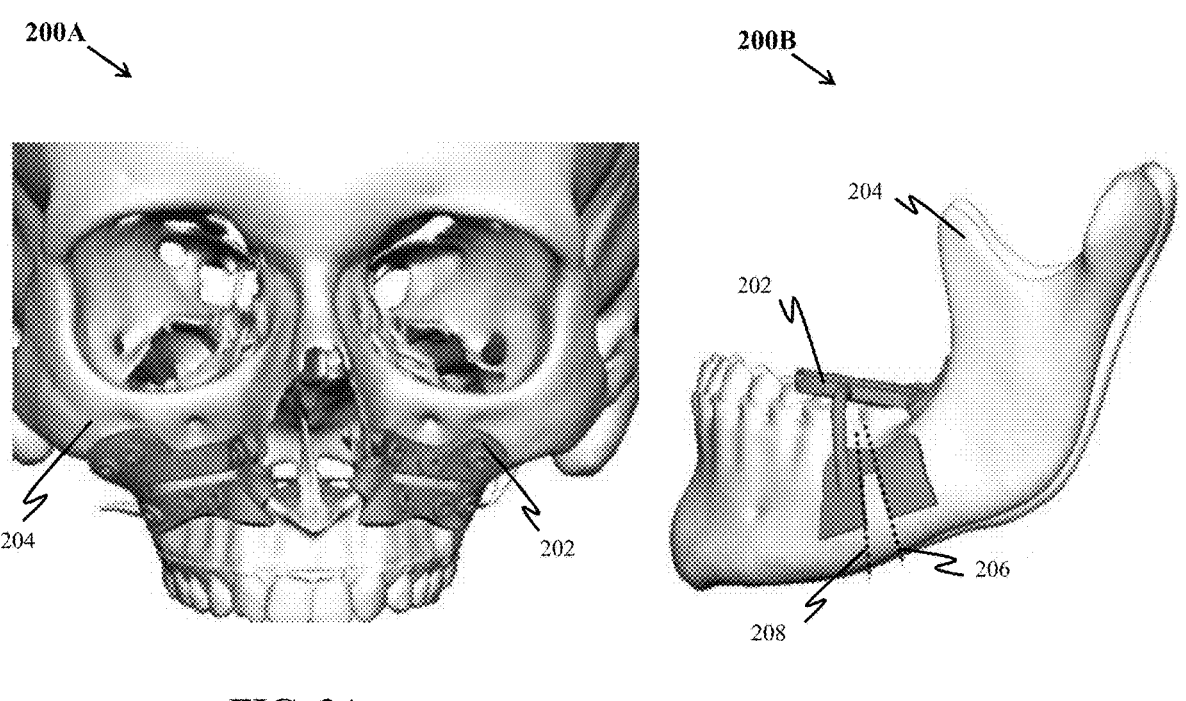
Figure 3A:
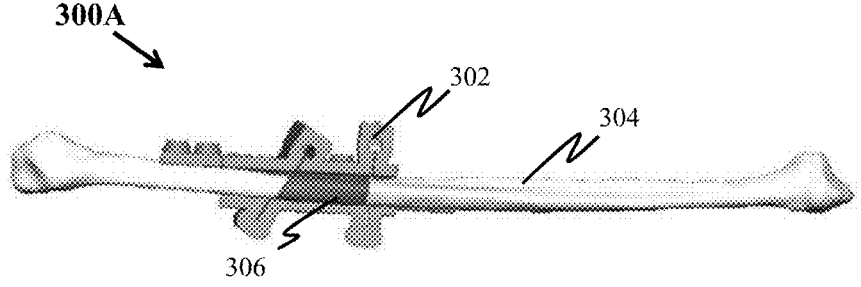
Figure 3B:
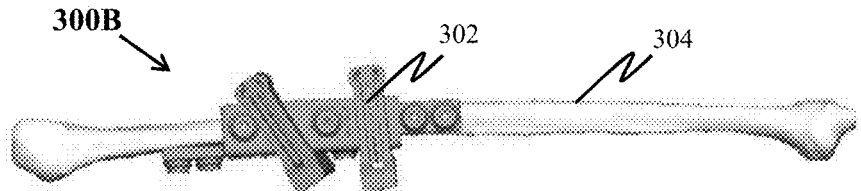
Figure 3C:
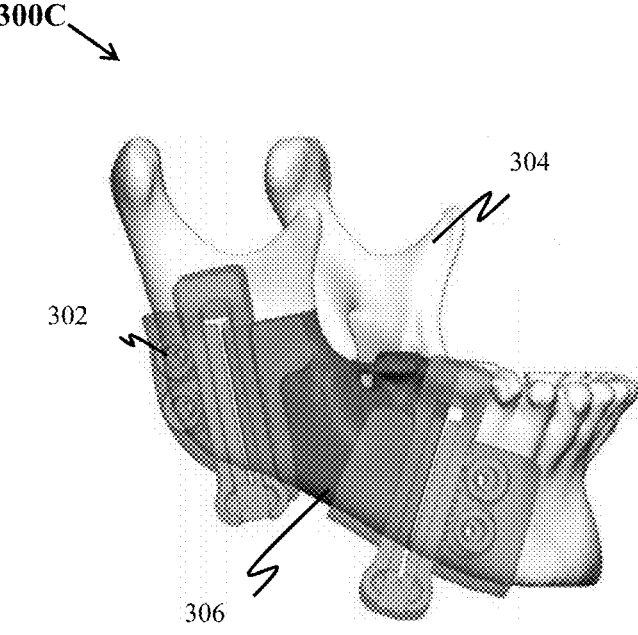
Figures 4A, 4B:
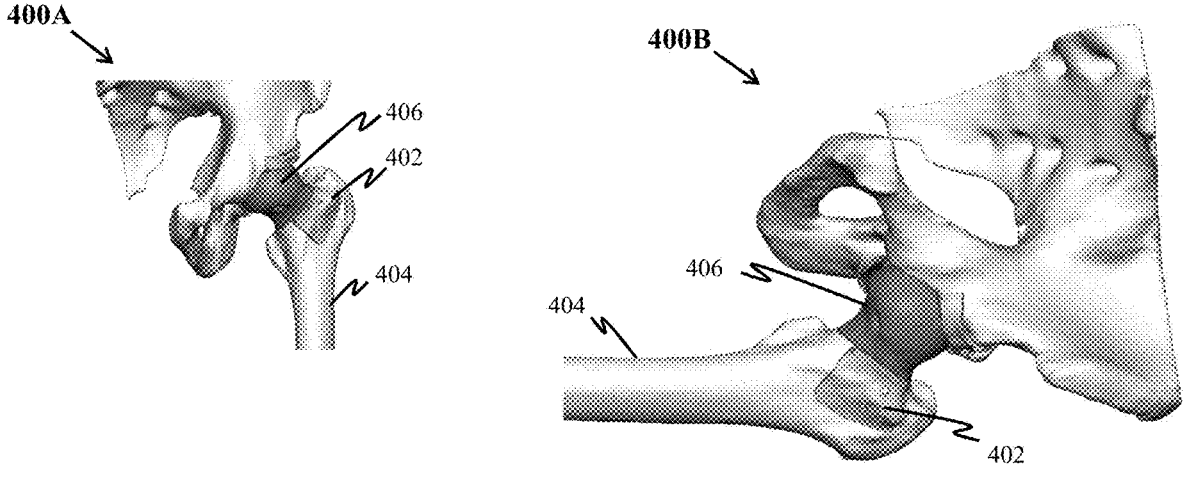
Figure 5:
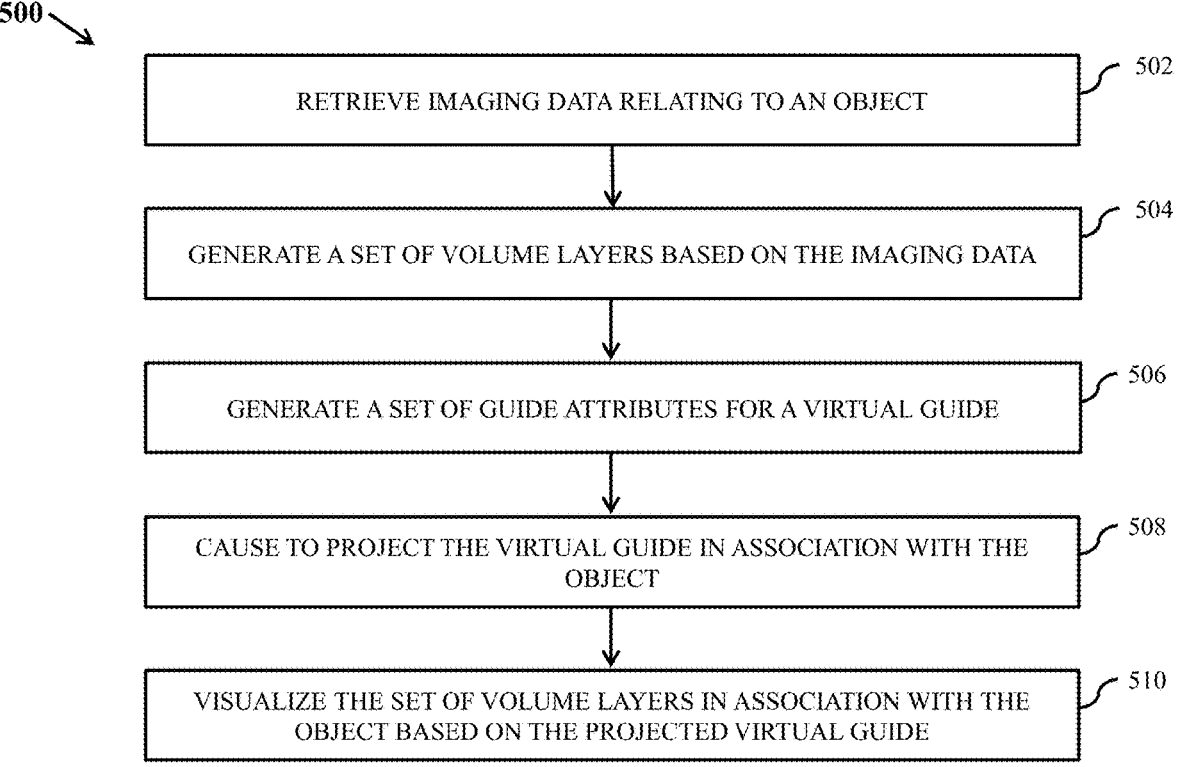

Having thus described example embodiments of the disclosure in general terms, reference will now be made to the accompanying drawings, which are not necessarily drawn to scale, and wherein:

FIG. 1A illustrates an exemplary environment in which a system for collocating a set of volume layers in association with an object is implemented, in accordance with an example embodiment;

FIG. 1B illustrates a block diagram of the system of FIG. 1, in accordance with an example embodiment;

FIG. 2A and FIG. 2B collectively illustrate positioning of a virtual guide on a biological structure, in accordance with an example embodiment;

FIG. 3A, FIG. 3B and FIG. 3C collectively illustrate positioning of a virtual guide on a biological structure, in accordance with an example embodiment;

FIG. 4A and FIG. 4B collectively illustrate positioning of a virtual guide on a biological structure, in accordance with an example embodiment; and FIG. 5 illustrates an example method for visualizing a set of volume layers with an objects in an immersive environment, in accordance with an example embodiment.

DETAILED DESCRIPTION

In the following description, for purposes of explanation, numerous specific details are set forth in order to provide a thorough understanding of the present disclosure. It will be apparent, however, to one skilled in the art that the present disclosure may be practiced without these specific details. In other instances, devices and methods are shown in block diagram form only in order to avoid obscuring the present disclosure.

Some embodiments of the present disclosure will now be described more fully hereinafter with reference to the accompanying drawings, in which some, but not all, embodiments of the disclosure are shown. Indeed, various embodiments of the disclosure may be embodied in many different forms and should not be construed as limited to the embodiments set forth herein; rather, these embodiments are provided so that this disclosure will satisfy applicable legal requirements. Like reference numerals refer to like elements throughout. Also, reference in this specification to "one embodiment" or "an embodiment" means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Further, the terms "a" and "an" herein do not denote a limitation of quantity, but rather denote the presence of at least one of the referenced item. Moreover, various features are described which may be exhibited by some embodiments and not by others. Similarly, various requirements are described which may be requirements for some embodiments but not for other embodiments. As used herein, the terms "data," "content," "information," and similar terms may be used interchangeably to refer to data capable of being displayed, transmitted, received and/or stored in accordance with embodiments of the present disclosure. Thus, use of any such terms should not be taken to limit the spirit and scope of embodiments of the present disclosure.

The embodiments are described herein for illustrative purposes and are subject to many variations. It is understood that various omissions and substitutions of equivalents are contemplated as circumstances may suggest or render expedient but are intended to cover the application or implementation without departing from the spirit or the scope of the present disclosure. Further, it is to be understood that the phraseology and terminology employed herein are for the purpose of the description and should not be regarded as limiting. Any heading utilized within this description is for convenience only and has no legal or limiting effect.

Definitions

The term "immersive environment" refers to a digital or artificial computer-created environment that completely engulfs senses of a user, typically through technologies such as virtual reality (VR), augmented reality (AR), mixed reality (MR), or even advanced physical installations like themed rooms or sensory chambers. The immersive environment creates a deeply engaging and realistic experience that transports the user to a different simulation environment, scenario, or world, allowing them to interact with their surroundings and/or virtual components in a highly immersive way.

The term "virtual reality" may refer to a simulated three-dimensional environment that enables users to explore and interact with a virtual surrounding in a way that approximates reality, as it is perceived through the users' senses.

The term "augmented reality" may refer to an integrated environment comprising digital information with a user's environment in real time. Unlike virtual reality (VR), which creates a totally artificial environment, augmented reality (AR) users experience a real-world environment with generated perceptual information (or virtual digital information) overlaid on top of it.

The term "mixed reality" refers to an integrated environment comprising a real-world environment merging with a computer-generated environment. In an example, an AR environment may be analogous to a mixed reality environment. In particular, physical and virtual objects may co-exist in mixed reality and AR environments and interact in real time.

The term "volume layers" may refer to a set of geometry that shares a same rendering material and source. In an example, the volume layers may be data layers comprising information relating to different elements of one or more images of a biological structure of a patient. In an example, the volume layers may be constructed either from an iso-surface contained in a scalar volume dataset, a signed distance field (SDF) of an editable volume object, or a binary volume dataset derived from volume segmentation. Multiple iso-surface layers may be created from the same volume dataset.

The term "virtual guide" refers to a virtual model of a guide. For example, the virtual guide may be an object-specific virtual model. In an example, the virtual guide may be a model that directs collocation or visualization of the volume layers in real world, such as on an object. In an example, the virtual guide may include model of the object-specific structure that may conform to a biological structure of a patient. The virtual guide may be positioned on the physical biological structure of the patient to enable certain operations accurately. For example, the virtual guide may be positioned in association with or on the biological structure of the patient to enable functions of marking and/or cutting during a surgery process accurately.

End of Definitions

A system, a method and a computer programmable product are provided herein in accordance with an example embodiment for visualizing a set of volume layers in association with an object accurately. The system, the method and the computer programmable product disclosed herein enables generating the set of volume layers based on object-specific imaging data and generating a virtual guide for collocating the set of volume layers in association with the object, such as a biological structure of a patient. In particular, the virtual guide may be positioned or projected on the biological structure for accurate positioning of the set of volume layers on the biological structure. This enables accurate tracking of movement of physical or virtual elements with respect to the object, i.e., the biological structure. In this manner, the set of volume layers that may be generated in VR environment may be visualized accurately in an AR environment, i.e., with the physical object, such as the biological structure and based on gestures and movements of a user.

Referring to FIG. 1, there is shown an exemplary environment 100A in which a system 102 for visualizing a set of volume layers in association with an object is implemented, in accordance with an example embodiment. In an example, the object is a biological structure 120 of a patient. The embodiments of the present disclosure are described with regard to implementation in medical industry, such as during surgeries. Subsequently, examples of objects for which visualization of volume layers is performed are biological structures. It may be noted that such examples of the object as the biological structures are only exemplary and should not be construed as a limitation. Those skilled in the art may realize that embodiments of the present disclosure may be used in other scenarios for visualization of volume layers with respect to different kinds of objects. Examples of fields associated with the different kinds of objects may include, but are not limited to, entertainment, gaming, training simulation, education, architecture design, marketing, retail, tourism, hospitality, art, and therapy and rehabilitation.

The system 102 includes a workstation 104A, a processor 104B, a display screen 106, and a set of keyboard and mouse 108. The system 102, specifically, the workstation 104A, is shown as being operated by two users depicted as, for example, user 110a and user 110b. In the illustrated example, the users 110a and 110b are wearing a display device 112, such as an AR/VR headset. The users 110a and 110b may use the display device 112 for viewing a stereoscopic visualization 114 of a set of volume layers relating to the biological structure 120 of the patient 124.

The system may also include or may be connected to a tracking object 116. Although the tracking object 116 is shown as a part of the system 102 in the present example, this should not be construed as a limitation. In certain cases, the system 102 may be remotely connected to the tracking object 116. In an example, the system 102 may be implemented as a hardware device. In another example, the system 102 may be implemented as a remote computing device performing its operations over cloud or other remote infrastructure, such that the visualization 114 generated by the system 102 is displayed using the display device 112.

In operation, the processor 104B is configured to retrieve imaging data relating to an object. According to the present example, the object is the biological structure 120 of the patient 124. In an example, the imaging data comprises patient's medical imaging data, such as CT, CTA, MRI, MRA, etc.

The processor 104B is configured to generate a set of volume layers corresponding to the object based on the imaging data. For example, the set of volume layers may relate to the biological structure 120, such as a skull of the patient 120. For example, each of the volume layers from the set of volume layers may include or depict certain elements of the imaging data relating to the biological structure 124. In other words, various elements of the imaging information of the patient may be included in different volume layers forming the set of volume layers. These set of volume layers may have to be transferred to an augmented reality platform or environment, i.e., collocate the set of volume layers with the patient specific anatomy on the biological structure 120 of the patient 124 to enable the users 110a and 110b to view the imaging data in an immersive environment, such as AR with greater accuracy.

First, the processor 104B is configured to generate a 3-dimensional (3D) array of voxels based on the imaging data. Each array of voxels may be used to create a volume layer from the set of volume layers. In an example, a total number of layers for a 3D array of the set of volume layers may be predefined, defined by the users 110a and 110b, or dynamically determined.

Further, the processor 104B is configured to generate a set of guide attributes associated with a virtual guide 118 for the object based on the imaging data. In an example, the virtual guide 118 includes an object-specific structure. For example, the virtual guide 118 is associated with the biological structure 120 and depicted as a scissor for performing a function associated with the object or the biological structure 120. In an example, the set of guide attributes associated with the virtual guide 118 are aligned with device attributes of the tracking object 116 and/or the display device 112. The set of volume layers may be one or more sets of 3D volume data or 2D image data and may be rendered by the system 102 in accordance with the disclosed principles. In the illustrated embodiment, a rendering of one or more 3D volume datasets or 2D image datasets in accordance with the disclosed principles may also be presented on the display screen 106.

In particular, to visualize the set of volume layers in association with the biological structure 120 of the patient 124 accurately, the virtual guide 118 may be required. In an example, the virtual guide 118 may be designed to work with the tracking object 116 and may have different modalities based on a visual fiducial system used by the tracking object 116. In an embodiment, the virtual guide 118 may be a constellation of spheres or other geometric primitives, a two-dimensional bar code, a constellation of 2D bar codes, a constellation of Quick Response (QR) codes, a 2D image, or a 3D object.

The processor 104B is configured to cause to project the virtual guide 118 at least in association with the object or the biological structure 120. The virtual guide 118 may be positioned or projected on one or more real objects of significance (such as the biological structure 120) and a display of the display device 112. In the illustrated embodiment, real objects of significance may be the biological structure 120 or one or more surgical instruments 122. Although the virtual object 118 is shown to be projected in association with the biological structure, this should not be construed as a limitation. In other examples, the virtual object 118 may be projected with reference to other real-world objects of significance, such as the surgical instruments 122. In an example, the virtual guide 118 is projected using a projection using associated with the system 102, the tracking object 116 or the display device 112.

In a medical environment, the virtual guide 118 may be custom designed. In an example, the virtual guide 118 may be a 3D model that is rendered on a fixture on the patient body, or directly to the biological structure 120 of the patient. For example, the biological structure 120 may be a bone, an organ, a tissue, and so forth. In certain cases, there may also be such virtual guide 118 projected onto a display of the display device 112.

Further, the processor 104B is configured to visualize the set of volume layers in association with the object, i.e., the biological structure 120, based on the projected virtual guide 118. In an example, a custom or patient-specific virtual guide 118 may be used to visualize the set of volume layers on the biological structure 120.

In accordance with an example embodiment, the processor 104B is further configured to determine tracking data associated with the users 110a and 110b with respect to the object, i.e., the biological structure 120, using the tracking object 116. In an example, the tracking object 116 is configured to track the projection of the virtual guide 118 in order to track positions, orientations, gestures etc. of the users 110a and 110b in real time. For example, such tracked positions, orientations, gestures etc. of the users 110a and 110b may form the tracking data associated with the users 110a and 110b. In other words, the tracking data of the users 110a and 110b includes location data, movement data, orientation data, and/or gestures data associated with the users 110a and 110b. In certain cases, the tracking object 116 is also configured to track positions, orientations, etc. of the display devices 112 of the users 110a and 110b based on tracking the virtual guide 118. In this regard, distance and spatial information of the users 110a and 110b as well as the display devices 112 are determined based on relative distance from the virtual guide 118.

To visualize the set of volume layers accurately on a patient anatomy or the biological structure 120 of the patient 124 with respect to the users 110a and 110b, the tracking object 116 may be required. In an example, the tracking object 116 may track location, movement, orientation, gestures, etc. of the users 110a and 110b. In an embodiment, the tracking object 116 may be a separate equipment that is physically or wirelessly connected with the system 102 or the processor 104B. In another embodiment, the tracking object 116 may be a software component that receives optical input data from existing optical sensors on the display devices 112 or any other devices of the system 102 or the workstation 104A.

Further, the processor 104B is further configured to cause to update the projection of the virtual guide 118. For example, a position, an orientation, etc. of the projection of the virtual guide 118 may be updated based on changes in position, orientation, etc., of the users 110a and 110b. Subsequently, the processor 104B is further configured to visualize the set of volume layers in association with the biological structure 120 based on the updated projection of the virtual guide 118.

In accordance with another example embodiment, the processor 104B is configured to determine interaction data between the users 110*a* and 110*b* and the visualized set of volume layers using the tracking object 116. In particular, the virtual guide 118 enables accurate tracking of an interaction between the users 110*a* and 110*b* and the set of volume layers. In particular, the virtual guide 118 connects with the tracking object 116 to enables the tracking object 116 to accurately track the interaction between the users 110*a* and 110*b*, the set of volume layers and the physical object, such as the biological structure 120, surgical equipment 122, etc.

In this regard, the processor 104B is configured to generate updated set of volume layers for the object or the biological structure 120 based on the imaging data and the interaction data. In an example, the processor 104B is configured to make modifications to the generated set of volume layers to generate the updated set of volume layers for the biological structure 120. The modifications may include, but are not limited to, creating new volume layers by separating an existing volume layer, adding hardware layers, adding measurement layers, add hardware trajectory layers, etc. All the modifications may be stored on a virtual reality platform.

Further, the processor 104B is configured to visualize the updated set of volume layers in association with the object or the biological structure 120 based on the projected virtual guide 118. The set of volume layers, including modified volume layers, may be saved in a format that is transferable to an augmented reality platform. The augmented reality platform may receive the set of volume layers as input and may display the set of volume layers via the display device 112. For example, the display device 112 may be a head-mounted display or AR headset. For example, the display device 112 may be an AR head-mountable display device, a VR head-mountable display device, or a MR head-mountable display device.

In accordance with an example embodiment, the processor 104B is configured to cause to project the virtual guide 118 on a display of the display devices 112 associated with the users 110*a* and 110*b*. In particular, the virtual guide 118 projected in association with the biological structure 120 is made visible to the users 110*a* and 110*b* using the display devices 112. Subsequently, the processor 104B is configured to cause to display the visualized set of volume layers, i.e., the visualization 114 on the display of the display device 112.

The display devices 112, such as AR/VR headset helps in viewing of the visualization 114 of the set of volume layers (such as, one or more sets of 3D volume data or 2D image data) associated with the biological structure 120. The visualization 114 may be in 2D or in 3D and may be viewed from different angles and positions. The visualization 114 of the set of volume layers may be projected onto the actual biological structure 120 of the patient 124 from which the data was previously scanned from. The visualization 114 may be superimposed on the corresponding actual biological structure 120 by collocating the 3D volume data or the 2D image data on the patient body.

In an example, the tracking object 116 reports tracking data and/or interaction data for all markers or objects of significance that it sees in an immersive environment, such as real-world environment and virtual environment. In an example, the markers may correspond to the virtual guide 118 rendered on the patient and/or other real world objects, physical biological structure, surgical equipment, users' movements, and so forth. For example, an offset between the virtual guide 118 and each of the objects of significance it's attached to, such as the biological structure 120, the stereoscopic visualization 114, the users 110*a* and 110*b*, and the one or more surgical instruments 122, is known ahead of time, based on a shape of the virtual guide 118 and position and orientation of the users 110*a* and 110*b*. Further, real-time offset between the objects and the virtual guide is continuously tracked. In this manner, the tracking object 116 determines the tracking data indicating changes in movement of the users 110*a* and 110*b* with respect to the virtual guide 118, and interaction data indicating interaction of the users 110*a* and 110*b* or other objects with the visualization 114 of the set of volume layers.

In an example, the processor 104B is configured to determine linear measurements, or angular measurements, with respect to at least the virtual guide 118, the object or the biological structure 120 and the visualization of the set of volume layers. For example, the offset, the tracking data and/or the interaction data may be determined based on linear and/or angular displacement of any real or virtual objects (such as, the users 110*a* and 110*b*, the display devices 112, the visualization 114 of the set of volume layers, surgical instrument 122, etc.) in the AR or VR environment with respect to the virtual guide 118.

In an example, the processor 104B is configured to generate a 3D model of the object or the biological structure 120 of the patient 124. In an example, the processor 104B is configured to generate the 3D model based on the imaging data, such that the 3D model may correspond to an outline of the biological structure 120. It may be noted that the imaging data corresponds to source 2D patient scans (such as CT, MRI, X-ray) corresponding to the biological structure 120. Further, the processor 104B is configured to visualize or overlay the set of volume layers corresponding to the biological structure 120 indicating the source 2D patient scans in association with the 3D model. For example, the visualization of the set of volume layers may be performed such that the volume layers are placed or overlaid within a boundary defined by the 3D model.

In this manner, a view perspective of the users 110*a* and 110*b* may be computed based on the tracked position and orientation of the display devices 112 of the users 110*a* and 110*b* and the virtual guide 118 as well as the offset between the display devices 112 and both eyes of the users 110*a* and 110*b*. In an example, the processor 104B uses these offsets, the virtual guide 118 and the set of volume layers to visualize volume layers for each rendered object or element in a correct location from a view perspective of the users 110*a* and 110*b*, allowing the stereoscopic visualization 114 of the 3D objects or 2D images to be superimposed to their real-world counterparts, such as the biological structure 120.

Subsequently, the set of volume layers relating to the biological structure 120 of the patient 124 may be visualized or collocated or overlaid on the biological structure 120 or any other real-world object or element, such as the one or more surgical instruments 122. To this end, rendering the virtual guide 118 on the biological structure 120 or the patient's body may improve the accuracy of visualization of the set of volume layers of the 3D objects or 2D images on the real-world counterparts, such as the biological structure 120. With more accurate visualization of the set of volume layers in the real-world, certain operations, such as a surgery process may be performed using the AR immersive environment.

For example, the virtual guide 118 may enable the users 110*a* and 110*b* to interact with the biological structure 120, the one or more surgical instruments 122, the patient 124, or any other object in real-world or virtual element, with greater ease and accuracy. A manner of use of the virtual guide 118 is described in detail in conjunction with the following FIG. 2A, FIG. 2B, FIG. 3A and FIG. 3B.

FIG. 1B illustrates a block diagram 100B of the system 102 of FIG. 1, in accordance with an embodiment of the disclosure. FIG. 2 is explained in conjunction with FIG. 1.

The system 102 may include one more processors (referred to as a processor 132, hereinafter), a non-transitory memory (referred to as a memory 134, hereinafter), an input/output (I/O) interface 136, and a communication interface 138. The processor 132 may be similar to the processor 104B. The processor 132 may further include an input module 132A, a volume layers generation module 132B, a virtual guide generation module 132C, and a visualization module 132D. The memory 134 may further include a set of volume layers 134A, and a set of guide attributes 134B. The processor 132 may be connected to the memory 134, the I/O interface 136, and the communication interface 138 through one or more wired or wireless connections. Although in FIG. 1B, it is shown that the system 102 includes the processor 132, the memory 134, the I/O interface 136, and the communication interface 138, however, the disclosure may not be so limiting and the system 102 may include fewer or more components to perform the same or other functions of the system 102.

The processor 132 of the system 102 may be configured to perform one or more operations associated with visualizing the set of volume layers 134A in association with an object, such as the biological structure 120 in an AR environment. The processor 132 may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application-specific integrated circuit), an FPGA (field programmable gate array), a microcontroller unit (MCU), a hardware accelerator, a special-purpose computer chip, or the like. As such, in some embodiments, the processor 132 may include one or more processing cores configured to perform independently. A multi-core processor may enable multiprocessing within a single physical package. Additionally, or alternatively, the processor 132 may include one or more processors configured in tandem via the bus to enable independent execution of instructions, pipelining, and/or multithreading. Additionally, or alternatively, the processor 132 may include one or more processors capable of processing large volumes of workloads and operations to provide support for big data analysis. In an example embodiment, the processor 132 may be in communication with the memory 134 via a bus for passing information among components of the system 102.

For example, when the processor 132 may be embodied as an executor of software instructions, the instructions may specifically configure the processor 132 to perform the algorithms and/or operations described herein when the instructions are executed. However, in some cases, the processor 132 may be a processor-specific device (for example, a mobile terminal or a fixed computing device) configured to employ an embodiment of the present disclosure by further configuration of the processor 132 by instructions for performing the algorithms and/or operations described herein. The processor 132 may include, among other things, a clock, an arithmetic logic unit (ALU), and logic gates configured to support the operation of the processor 132.

The memory 134 may be non-transitory and may include, for example, one or more volatile and/or non-volatile memories. In other words, for example, the memory 134 may be an electronic storage device (for example, a computer readable storage medium) comprising gates configured to store data (for example, bits) that may be retrievable by a machine (for example, a computing device like the processor 132). The memory 134 may be configured to store information, data, content, applications, instructions, or the like, for enabling the system 102 to carry out various operations in accordance with embodiments of the present disclosure. For example, the memory 134 may be configured to buffer input data for processing by the processor 132. As exemplified in FIG. 1B, the memory 134 may be configured to store instructions for execution by the processor 132. As such, whether configured by hardware or software methods, or by a combination thereof, the processor 132 may represent an entity (for example, physically embodied in circuitry) capable of performing operations according to an embodiment of the present disclosure while configured accordingly. Thus, for example, when the processor 132 is embodied as an Application Specific Integrated Circuit (ASIC), Field Programmable Gate Array (FPGA), or the like, the processor 132 may be specifically configured hardware for conducting the operations described herein. In an embodiment, memory 134 may be configured to store the set of volume layers 134A and the set of guide attributes 134B, among other data generated during execution of the operations or instruction by the processor 132 for visualizing the set of volume layers 134A.

In some example embodiments, the I/O interface 136 may communicate with the system 102 and display, such as the display screen 106 and input and/or output, such as the keyboard and mouse 108 of the system 102. As such, the I/O interface 136 may include a display and, in some embodiments, may also include a keyboard, a mouse, a touch screen, touch areas, soft keys, or other input/output mechanisms. In one embodiment, the system 102 may include a user interface circuitry configured to control at least some functions of one or more I/O interface elements such as the display and, in some embodiments, a plurality of speakers, a ringer, one or more microphones and/or the like. The processor 132 and/or I/O interface 136 circuitry including the processor 132 may be configured to control one or more operations of one or more I/O interface 136 elements through computer program instructions (for example, software and/or firmware) stored on the memory 134 accessible to the processor 132.

The communication interface 138 may include the input interface and output interface for supporting communications to and from the system 102 or any other component with which the system 102 may communicate. The communication interface 208 may be any means such as a device or circuitry embodied in either hardware or a combination of hardware and software that is configured to receive and/or transmit data to/from a communications device in communication with the system 102. In this regard, the communication interface 208 may include, for example, an antenna (or multiple antennae) and supporting hardware and/or software for enabling communications with a wireless communication network. Additionally, or alternatively, the communication interface 138 may include the circuitry for interacting with the antenna(s) to cause transmission of signals via the antenna(s) or to handle receipt of signals received via the antenna(s). In some environments, the communication interface 138 may alternatively or additionally support wired communication. As such, for example, the communication interface 138 may include a communication modem and/or other hardware and/or software for supporting communication via cable, digital subscriber line (DSL), universal serial bus (USB), or other mechanisms.

The communication interface 138 of the system 102 may be used to access a communication network. The communication network may include a communication medium through which the system 102 and, for example, the tracking object 116 and the display device 112, may communicate with each other. The communication network may be one of a wired connection or a wireless connection. Examples of the communication network may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the network environment 100 may be configured to connect to the communication network in accordance with various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), a device to device communication, cellular communication protocols, and Bluetooth (BT) communication protocols.

In one embodiment, the processor 132 may include the input module 132A. The input module 132A may be configured to receive, obtain, or retrieve input data associated with the system 102. In an example, the input data may include the imaging data associated with the patient 124, specifically the biological structure 120 of the patient 124. In certain cases, the input data may also include tracking data and interaction data that may be determined by the tracking object 116 and transmitted to the system 102. The input module 132A may retrieve or receive the tracking data and the interaction data from the tracking object 116.

In another embodiment, the processor 132 may include the volume layers generation module 132B. In an example, the volume layers generation module 132B is configured to generate the set of volume layers 134A corresponding to 3D objects or 2D images of real-world, such as the biological structure 120. In an example, each layer of the set of volume layers may include a 3-dimensional (3D) or a 2-dimensional (2D) array of voxels based on the imaging data. For example, each layer of the set of volume layers may represent a distinct region or volume within a 3D environment and may contain different elements or attributes associated with the object in the 3D environment.

In yet another embodiment, the processor 132 may include the virtual guide generation module 132C. In an example, the virtual guide generation module 132C is configured to generate the set of guide attributes 134B associated with the virtual guide 118. For example, the set of guide attributes 134 corresponding to the virtual guide 118 includes object-specific information. In an example, the set of guide attributes 134 corresponding to the virtual guide 118 may include the patient-specific attributes or the biological structure 120 specific attributes. In an example, the set of guide attributes 134B may include dimensional information, shape information, structure information, etc. associated with the object or the biological structure 120 of the patient 124. Based on the set of guide attributes 134, the virtual guide 118 may be generated. In an example, the processor 132 may cause to project the virtual guide 118 in association with the object or the biological structure 120.

In an example, the virtual guide generation module 132C is also configured to generate updated set of guide attributes based on the tracking data received from the tracking object 116. For example, the tracking data may indicate a change in position, orientation, gesture etc. of the users 110a and 110b with respect to the virtual element 118. In particular, the change may be determined based on an offset of the users 110a and 110b from the virtual object 118. Subsequently, the virtual guide generation module 132C is configured to generate updated set of guide attributes for an updated location or position of the virtual guide 118 in the AR environment. Subsequently, the processor 132 may cause to update the projection of the virtual guide 118 based on the updated set of guide parameters.

In another embodiment, the processor 132 may include the visualization module 132D. In an example, the visualization module 132D is configured to generate the visualization 114 of the object or the biological structure 120 based on the set of volume layers 134A and the virtual guide 118. In an example, the visualization module 132D is configured to localize or collocate the set of volume layers 134A with the biological structure 120 to generate the visualization 114. Such visualization 114 may be projected in association with the biological structure 120 using a display of the display device 112 of the users 110a and 110b.

In an example, the volume layers generation module 132B is also configured to generate updated set of volume layers based on the interaction data received from the tracking object 116. For example, the interaction data may indicate a manner in which the users 110a and 110b may interact with currently projected visualization of the set of volume layers in the AR environment. In particular, the interaction may be determined based on an offset of the users 110a and 110b from the virtual object 118 and the visualization 114. Subsequently, the virtual volume layers generation module 132B is configured to generate the updated set of volume layers for an updated visualization of the biological structure 120 in the AR environment. Subsequently, the visualization module 132D may visualize the updated set of volume layers in association with the biological structure 120 based on the projected virtual guide 118.

FIG. 2A illustrates a perspective view 200A of projection of a virtual guide 202 on a biological structure 204, in accordance with an example embodiment. Further, FIG. 2B illustrates a side view 200B of the projection of the virtual guide 202 on the biological structure 204, in accordance with an example embodiment. In an example, the biological structure 204 may be a real-world or a physical entity, such as the biological structure 120. In other examples, the virtual guide 202 may be projected with other real-world objects, such as the one or more surgical instruments 122, the patient 124, or any other object in real-world.

In an example, the processor 132 is configured to generate the set of guide attributes 134B for the virtual guide 202 based on object-specific imaging data, i.e., patient-specific imaging data in the present case. In an example, the virtual guide 202 may correspond to the biological structure 204 of the patient. For example, the set of guide attributes 134B may include, but is not limited to, dimension information, shape information, patient details, and other information specific to the patient and the biological structure 204. Pursuant to present example, the set of guide attributes 134B may include patient-specific information relating to bone overlap osteotomy plane 206 and BSSO osteotomy plane 208.

Based on the set of guide attributes 134B, the virtual guide 202 may be generated. For example, the virtual guide 202 may be a 3D model based on the set of guide attributes 134B. In an example, the virtual guide 202 is generated based on three-dimensional (3D) printing of the set of guide attributes 134B in a virtual environment. Once generated, the virtual guide 202 may be rendered in association with the biological structure 204, such as on the biological structure 204 or at a particular position with respect to the biological structure 204.

As shown in FIGS. 2A and 2B, the virtual guide 202 may be patient-specific virtual or digital model used as a marking guide. In particular, the virtual guide 202 may be used to provide a reference to where a function may be performed. In an example, the function is related to a surgery operation, a treatment operation, or a diagnostic operation. Such function may include, but are not limited to, hole, cut, drill, puncture, and the like.

In operation, the processor 132 may cause to project or render the virtual guide 202 in association with the biological structure 204 of the patient. In an example, the virtual guide 202 may have one or more parts. Such different parts of the virtual guide are rendered accurately on the biological structure 204 in association with each other.

In accordance with an example embodiment, the processor 132 may be configured to receive marking data relating to the object or the biological structure 204. In an example, the marking data corresponds to a function. Moreover, the marking data is associated with the virtual guide 202. In an example, the users 110a or 110b may create markings for where the function is to be performed using the rendered virtual guide 202. Such data may be collected as the marking data using the tracking object or optical sensors of the display device 112.

Further, the processor 132 may be configured to visualize the set of volume layers 134A in association with the object or the biological structure 204 based on the virtual guide 202 and the marking data. For example, the virtual guide 202 may also be used to render other elements of a virtual environment, for example, as the set of volume layers 134A. In an example, the set of volume layers 134A may depict the biological structure 204. In such a case, based on the virtual guide 202, the set of volume layers 134A may be rendered on the biological structure 204. Further, the set of volume layers 134A visualized to include information of the marking data.

The processor 132 is further configured to cause to perform the function based on the visualized the set of volume layers 134A. For example, the users 110a and 110b may perform the function based on the volume layers 134A which is visualized based on the marking data. For example, when a marking data indicates a mark or a point for incision, the set of volume layers 134A is visualized along with the marking data. In such a case, the mark or a point for incision may be displayed in conjunction with the volume layers 134A of the biological structure 204. Based on the displayed mark or point, the function of incision may be performed.

It may be noted, the virtual guide 202 may be generated based on the attributes of VR environment, i.e., the imaging data of the patient 124. Based on the imaging data of the patient in VR, the set of volume layers 134A may also be generated. Such set of volume layers 134A of the biological structure 204 in the virtual environment may be localized or visualized in conjunction with the real-world biological structure 204 using the virtual guide 202 and the tracking object 116. The virtual guide 202 and the tracking object 116 may accurately detect interaction between the users 110a and 110b, the biological structure 204, the virtual guide 202, and other elements in the VR or AR environment and the real-world environment. Based on such tracking, a projection of the virtual guide 202 and/or the visualization 114 of the set of volume layers 134A may be adjusted. Accordingly, owing to changes in position and orientation of render of the virtual guide 202, the set of volume layers 134A may also be adjusted.

In an example, the processor 132 may also include an AI module. The processor 132 may be configured to perform 3D landmark detection or 3D segmentations associated with the object or the biological structure 120 using the AI module. In an example, the 3D landmark detection or 3D segmentations may be performed in an automated or semi-automated manner using deep-learning assisted AI module. For example, the 3D landmark detection may be performed to identify real or virtual objects of significance for building the VR or AR environment. Further, 3D segmentations may be performed to partition the object under consideration, such as the biological structure 120 into partitions for generation of the corresponding set of volume layers, and visualization of the set of volume layers in segmented manner. For example, the segmentation may be performed based on certain characteristics, such as intensity, color, texture, or shape.

FIG. 3A illustrates a side view 300A of positioning of a virtual guide 302 on a biological structure 304, in accordance with an example embodiment. Further, FIG. 3B illustrates a top view 300B of positioning of the virtual guide 302 on the biological structure 304, in accordance with an example embodiment. FIG. 3C illustrates a perspective view 300C of positioning of the virtual guide 302 on the biological structure 304, in accordance with an example embodiment. In an example, the biological structure 304 may be a real-world or a physical entity. Pursuant to the present example, the biological structure 304 may correspond to facial bone anatomy. It may be noted that such depiction of the biological structure 304 corresponding to the facial bone is only exemplary and should not be construed as a limitation. In other embodiments of the present invention, the biological structure 304 may correspond to other anatomical part of a patient, or any other real-world object.

In an example, the virtual guide 302 is patient specific model. For example, the virtual guide 302 may be an operation guide for, for example, cutting, drilling, puncturing, and so forth. In an example, the virtual guide 302 may be used for cutting an anatomical part of the biological structure 304. In this regard, the processor 104B may display an anatomical render 306 of the anatomical part of the biological structure 304 that is to be cut or removed. An anatomical part corresponding to the anatomical render 306 may have to be removed as part of a surgical process or function. For example, a cutting plane of the virtual guide 302 may be based on marking data including a marking generated using the virtual guide 302 around the anatomical part. In an example, the marking or the marking data may be generated by the users 110a and 110b. Alternatively, the marking or the marking data may be generated based on a type of function, such as a type of surgery to be performed and pre-acquired information associated with the patient 124. The virtual guide 302 may enable a higher precision where cut is required.

For example, the virtual guide 302 may be positioned in association with the biological structure 304. In an example, the virtual guide 302 may be rendered to the biological structure 304 using, for example, interlocking joints, and so forth. Once the virtual guide 302 is rendered into place, the anatomical render 306 of the anatomical part that is to be removed may be used to understand what part of the biological structure 304 needs to be removed even before the users 110*a* and/or 110*b* makes a cut on the real object or the real biological structure 304. The virtual guide 302 and the anatomical render 306 enable to improve the accuracy of the surgical operation.

In an example, a same virtual guide may be used for marking and cutting. In another example, different patient-specific virtual guides may be used for creating marking lines and performing an operation or function, such as cutting based on the created marking lines.

FIG. 4A illustrates a front view 400A of positioning of a virtual guide 402 on a biological structure 404, in accordance with an example embodiment. Further, FIG. 4B illustrates a perspective view 400B of positioning of the virtual guide 402 on the biological structure 404, in accordance with an example embodiment. In an example, the biological structure 404 may be a real-world or a physical entity. Pursuant to the present example, the biological structure 404 may correspond to hip bone anatomy.

In an example, the virtual guide 402 is patient specific model. For example, the virtual guide 402 may be an operation guide for, for example, cutting, drilling, puncturing, and so forth. In an example, the virtual guide 402 may be used for cutting an anatomical part of the biological structure 404. Subsequently, the processor 104B may display an anatomical render 406 of the anatomical part of the biological structure 404 that is to be cut or removed. The anatomical part may have to be removed as part of a surgical process or operation. Further, a cutting plane of the virtual guide 402 may be based on marking data generated using the virtual guide 402 around the anatomical part. The virtual guide 402 may enable a higher precision where cut is required.

For example, the virtual guide 402 may be positioned in association with the biological structure 404. In an example, the virtual guide 402 may be rendered to the biological structure 404 using, for example, screws, interlocking joints, and so forth. Once the virtual guide 402 is rendered into place, the anatomical render 406 of the anatomical part that is to be removed may be used to understand what part of biological structure 404 needs to be removed even before the users 110*a* and/or 110*b* makes a cut. The virtual guide 402 and the anatomical render 406 enable to improve the accuracy of the surgical operation.

Referring to FIG. 5, there is shown a flowchart 500 of an example method for visualizing a set of volume layers in association with an object, in accordance with an example embodiment. Fewer, more, or different steps may be provided.

In an example, the method 500 may be implemented by the processor 104B or 132 on the workstation 104A. of the system 102. In another example, the method 500 may be implemented by a remote system 102 that may be communicatively connected to the display device 112 and the tracking object 116.

At 502, imaging data relating to an object is retrieved. In accordance with an example, the processor 132 or the input module 132A is configured to retrieve the imaging data. In an example, the imaging data may relate to the biological structure 120 of the patient 124. In an example, the imaging data may indicate a set of attributes relating to the biological structure of the patient. For example, the imaging data includes patient's medical imaging data. Examples of the medical imaging data may include, but are not limited to, Computed Tomography (CT) data, Computed Tomography Angiography (CTA) data, Magnetic Resonance Imaging (MRI) data, and Magnetic Resonance Angiography (MRA) data.

At 504, a set of volume layers is generated, based on the imaging data. In accordance with an example, the processor 132 or the volume layers generation module 132B is configured to generate the set of volume layers 134A based on the imaging data. The set of volume layers 134A may correspond to the virtual reality environment. For example, the set of volume layers 134A may indicate the biological structure 120 of the patient 124.

At 506, a set of guide attributes is generated for a virtual guide, based on the imaging data. In accordance with an example, the processor 132 or the virtual guide generation module 132C is configured to generate the set of guide attributes 134B based on the imaging data. In an example, the set of guide attributes 134B may include dimensional information, shape information, structure information, etc. In addition, the set of guide attributes 134B may include marking data for a function or an operation to be performed relating to the biological structure 120 or a part thereof. For example, the set of guide attributes 134B may include marking guide and cutting guide for performing a surgery operation.

At 508, a virtual guide is projected. In an example, the projector 132 is configured to cause to project the virtual guide 118 in association with the object or the biological structure 120 based on the set of guide attributes 134B. Based on the set of guide attributes 134B, the virtual guide 118 may be generated and projected. For example, the virtual guide 118 may be a 3D model depicting a marking guide and/or a cutting guide.

At 510, the set of volume layers is visualized in association with the object. In accordance with an embodiment, the processor 132 or the visualization module 132D is configured to generate the visualization 114 in association with the biological structure 120 of the patient 124 based on the virtual guide 118 and the se of volume layers 134A. In particular, the set of volume layers 134A may be overlaid on the biological structure 120 using the virtual guide 118 such that the virtual guide 118 enables accurate interaction between the AR environment and the real-world objects or the biological structure 120 and the surgical instruments 122. In an example, the virtual guide 118 may be a marking guide and/or a cutting guide. This may enable the users 110*a* and 110*b* to accurately perform operations, such as cutting, drilling, insertion, puncturing, etc., based on the visualization 114 as well as the virtual guide.

Accordingly, blocks of the method support combinations of means for performing the specified functions and combinations of operations for performing the specified functions. It will also be understood that one or more blocks of the method can be implemented by special purpose hardware-based computer systems which perform the specified functions, or combinations of special purpose hardware and computer instructions.

Alternatively, a system may comprise means for performing each of the operations described above. In this regard, according to an example embodiment, examples of means for performing operations may comprise, for example, a processor and/or a device or circuit for executing instructions or executing an algorithm for processing information as described above.

On implementing the method disclosed herein, the end result generated by the processor 104B or 132 is a tangible and accurate collocation of VR environment on real-world objects, i.e., the se of volume layers on the biological structure 120 for surgery process. This accurate collocation or visualization of VR elements or volume layers with real-world elements is crucial for performing the surgery, such as marking a target location and performing a function (such as cut, drill, puncture, etc.) at the target location accurately using the VR objects, such as the visualization 114.

The collocation or visualization techniques disclosed in the present disclosure provides capability to plan the surgery process with depth perception in virtual reality space, and capability to easily transfer the set of volume layers from virtual reality environment to the augmented reality environment. Further, procedural time of the surgery process may be reduced, intra-operative radiation on the patient may decrease, and accuracy of the pre-operative planning may improve. In addition, the collocation or visualization techniques may improve training methods for students and practitioners of such surgery process. Moreover, visualization of surgical stages during the surgery process may be improved. For example, the portability of the workstation 104A and the processor 104B may make the process less cumbersome and more efficient, allowing easy packing and unpacking of the setup. In addition, as the virtual guide is a digital model, a hardware may not be required for collocating the volume layers in AR environment.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the present disclosure. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the present disclosure. In this regard, for example, different combinations of elements and/or functions than those explicitly described above are also contemplated as may be set forth in some of the embodiments of the present disclosure. Although specific terms are employed herein, they are used in a generic and descriptive sense only and not for purposes of limitation.

What is claimed is:

1. A system, comprising:
a memory configured to store computer executable instructions; and
one or more processors configured to execute the instructions to:
retrieve imaging data of an object;
generate a set of volume layers of the object based on the imaging data;
generate a set of guide attributes for the object based on the imaging data;
generate a virtual guide based on the generated set of guide attributes, the virtual guide comprising a marking for a surgical process;
cause to project the virtual guide on a display of a display device, wherein the virtual guide is projected at a particular position with respect to the object;
cause to visualize the set of volume layers on the display based on the projected virtual guide, wherein the visualized set of volume layers are overlaid on the object.

2. The system of claim 1, wherein the set of guide attributes are aligned with device attributes of at least one of: a tracking object, or a display device.

3. The system of claim 2, wherein the one or more processors are further configured to execute the instructions to:
determine, using the tracking object, tracking data associated with a user with respect to the object;
cause to update the projection of the virtual guide; and
visualize the set of volume layers in association with the object based on the updated projection of the virtual guide.

4. The system of claim 3, wherein the tracking data of the user comprises at least one of: location data, movement data, orientation data, or gestures data.

5. The system of claim 2, wherein the one or more processors are further configured to execute the instructions to:
determine, using the tracking object, interaction data between a user and the visualized set of volume layers;
generate updated set of volume layers for the object based on the imaging data and the interaction data; and
visualize the updated set of volume layers in association with the object based on the projected virtual guide.

6. The system of claim 2, wherein the one or more processors are further configured to execute the instructions to:
cause to project the virtual guide on a display of the display device associated with a user; and
cause to display the visualized set of volume layers on the display of the display device.

7. The system of claim 2, wherein the display device is at least one of: an augmented reality (AR) head-mountable display device, a virtual reality (VR) head-mountable display device, or a mixed reality (MR) head-mountable display device.

8. The system of claim 1, further comprising an artificial intelligence (AI) module, wherein the one or more processors are further configured to execute the instructions to:
perform, using the AI module, at least one of: 3D landmark detection or 3D segmentations associated with the object.

9. The system of claim 1, wherein the one or more processors are further configured to execute the instructions to determine at least one of: linear measurements, or angular measurements, with respect to at least the virtual guide, the object and the visualization of the set of volume layers.

10. The system of claim 1, wherein each layer of the set of volume layers includes a 3-dimensional (3D) or a 2-dimensional (2D) array of voxels based on the imaging data.

11. The system of claim 1, wherein the object is a biological structure of a patient.

12. The system of claim 11, wherein the imaging data corresponds to source 2D patient scans, and wherein one or more processors are further configured to execute the instructions to:
generate a 3D model of the biological structure of the patient; and
visualize the set of volume layers corresponding to the biological structure indicating the source 2D patient scans in association with the 3D model.

13. The system of claim 1, wherein the virtual guide includes at least one of: a constellation of spheres or other geometric primitives, a two-dimensional (2D) bar code, a constellation of 2D bar codes, a constellation of Quick Response (QR) codes, a 2D image, or a 3D object.

14. The system of claim 1, wherein the set of guide attributes corresponding to the virtual guide includes object-specific information.

15. The system of claim 1, wherein the one or more processors are further configured to execute the instructions to:

receive marking data relating to the object, wherein the marking data corresponds to a function, and wherein the marking data is associated with the virtual guide;

visualize the set of volume layers in association with the object based on the virtual guide and the marking data; and cause to perform the function based on the visualized the set of volume layers.

16. The system of claim 1, wherein the system is related to at least one of: a surgery operation, a treatment operation, or a diagnostic operation.

17. A method, comprising:

retrieving imaging data of an object;

generating a set of volume layers of the object based on the imaging data;

generating a set of guide attributes for the object based on the imaging data;

generating a virtual guide based on the generated set of guide attributes, the virtual guide comprising a marking for a surgical process;

causing to project the virtual guide on a display of a display device, wherein the virtual guide is projected at a particular position with respect to the object; and

visualizing the set of volume layers on the display based on the projected virtual guide, wherein the visualized set of volume layers are overlaid on the object.

18. The method of claim 17, wherein the set of guide attributes are aligned with device attributes of at least one of: a tracking object, or a display device.

19. The method of claim 17, further comprising:

causing to display the visualized set of volume layers on the display of the display device.

20. A computer programmable product comprising a non-transitory computer readable medium having stored thereon computer executable instructions, which when executed by one or more processors, cause the one or more processors to carry out operations comprising:

retrieving imaging data of an object;

generating a set of volume layers of the object based on the imaging data;

generating a set of guide attributes for the object based on the imaging data;

generating a virtual guide based on the generated set of guide attributes, the virtual guide comprising a marking for a surgical process;

causing to project the virtual guide on a display of a display device, wherein the virtual guide is projected at a particular position with respect to the object; and visualizing the set of volume layers on the display based on the projected virtual guide, wherein the visualized set of volume layers are overlaid on the object.

\* \* \* \* \*